(12) United States Patent
Chan

(10) Patent No.: US 9,735,798 B2
(45) Date of Patent: Aug. 15, 2017

(54) PRECISION BIPOLAR CURRENT-MODE DIGITAL-TO-ANALOG CONVERTER

(71) Applicant: Xagenic Inc., Toronto (CA)

(72) Inventor: Wen Chan, Ontario (CA)

(73) Assignee: Xagenic Inc., Toronto (CA)

( * ) Notice: Subject to any disclaimer, the term of this patent is extended or adjusted under 35 U.S.C. 154(b) by 360 days.

(21) Appl. No.: 14/454,685

(22) Filed: Aug. 7, 2014

(65) Prior Publication Data

US 2015/0041317 A1 Feb. 12, 2015

Related U.S. Application Data

(60) Provisional application No. 61/863,403, filed on Aug. 7, 2013.

(51) Int. Cl.
*H03M 1/66* (2006.01)
*G01N 27/327* (2006.01)
*H03M 1/06* (2006.01)

(52) U.S. Cl.
CPC .......... *H03M 1/66* (2013.01); *G01N 27/3275* (2013.01); *H03M 1/0607* (2013.01)

(58) Field of Classification Search
CPC ... H03M 1/66; H03M 1/0607; G01N 27/3275
USPC ................................. 341/144, 127
See application file for complete search history.

(56) References Cited

U.S. PATENT DOCUMENTS

| 4,431,986 | A | * | 2/1984 | Haque | H03M 1/74 341/127 |
| 4,473,818 | A | * | 9/1984 | Youngquist | H03M 1/74 341/127 |
| 4,644,325 | A | | 2/1987 | Miller | |
| 4,829,236 | A | | 5/1989 | Brenardi et al. | |
| 4,853,698 | A | * | 8/1989 | Roessler | H03M 1/804 341/144 |
| 5,818,377 | A | * | 10/1998 | Wieser | H03M 1/0665 341/143 |
| 2003/0132195 | A1 | | 7/2003 | Edamura et al. | |

OTHER PUBLICATIONS

International Search Report and Written Opinion for PCT/US2014/50241 dated Nov. 6, 2014.
(Continued)

*Primary Examiner* — Brian Young

(57) ABSTRACT

A precision bipolar digital-to-analog converter (DAC) that provides a bipolar current output having a substantially fixed zero center point is provided. The DAC includes digital-to-analog converter circuitry configured to provide, responsive to a reference signal indicative of the digital data, a first analog current signal having a first potential and a second analog current signal having a second potential, subtractor circuitry configured to provide a bipolar current signal by subtracting the second analog current signal from the first analog current signal, the bipolar current signal having a zero center point, and first control circuitry electrically coupled to the subtractor circuitry and to the digital-to-analog converter circuitry, and configured to modify the second potential so that the second potential equals the first potential.

27 Claims, 7 Drawing Sheets

(56) References Cited

OTHER PUBLICATIONS

Chen et al., "A 6-bit Current-Steering DAC With Compound Current Cells for Both Communication and Rail-to-Rail Voltage-Source Applications," IEEE Transactions on Circuits and Systems II: Express Briefs, IEEE, US, Nov. 1, 2012, 5 pages.

Lin, et al., "A Precise Current Subtractor Design," 2011 International Conference on Circuits, System and Simulation, vol. 7, May 29, 2011, 5 pages.

Extended Search Report for European Patent Application No. 14835318.8, dated Mar. 10, 2017, 11 pages.

* cited by examiner

PRECISION BIPOLAR CURRENT-MODE DIGITAL-TO-ANALOG CONVERTER

CROSS-REFERENCE TO RELATED APPLICATIONS

This application claims the benefit of U.S. Provisional Application No. 61/863,403, filed on Aug. 7, 2013, which is hereby incorporated herein by reference in its entirety.

BACKGROUND

A common task in electronics design is the conversion of digital signals to their analog equivalents for the purpose of controlling various systems. For example, in a medical diagnostic device, a digital-to-analog converter (DAC) may be used to control the signal sweep applied to a sample being tested by electrochemical detection. Because accurate detection of the target analyte depends critically on the ability of the device to detect a reaction at specific signal amplitudes, it is important that the control circuitry (and hence the DAC) used to control the signal sweep apply precise signal amplitudes to the test sample. However, manufacturing and other defects in real-world components introduce errors, both systematic and stochastic, in the conversion process. In many digital to analog conversion architectures (especially those with bipolar outputs), costly trimming steps, more expensive precision components, additional equipment costs on the production line, or extensive calibration is required to improve the accuracy of the center or zero point, in order to obtain the desired precision. If the output is not centered on zero, a digital input of zero could produce a non-zero analog output. Such trimming not only adds to the cost of the DAC, but also compromises the stability of the DAC over time, as the trim itself degrades over time due to drift caused by temperature, component aging, and power supply variations. The human input factor required to select trimming elements also make high volume production of the DAC difficult.

SUMMARY

Disclosed herein are systems, devices, and methods for a precision bipolar digital-to-analog converter (DAC) that provides a bipolar current output having a substantially fixed zero center point. In certain embodiments, the precision DAC subtracts the positive complementary current outputs of a conventional DAC from each other to provide a bipolar current output. Such a subtraction allows a bipolar output to be achieved from a pair of unipolar current outputs without offsetting the potentials of the current output pins or level-shifting the final output, which could require additional trimming steps or reduce conversion accuracy.

In one aspect, a precision digital-to-analog converter (DAC) for converting digital data to a an analog output signal (e.g., a bipolar analog output) includes digital-to-analog converter circuitry configured to provide, responsive to digital data (e.g., a digital signal input), a first analog current signal having a first potential and a second analog current signal having a second potential, subtractor circuitry configured to provide a bipolar current signal by subtracting the second analog current signal from the first analog current signal, the bipolar current signal having a zero center point, and first control circuitry electrically coupled to the subtractor circuitry and to the digital-to-analog converter circuitry, and configured to modify the second potential so that the second potential equals the first potential. In some embodiments, the first potential is set by a voltage source (e.g., an external circuit) external to the DAC. The voltage source may be, for example, from an input stage of a circuit block that receives the analog output signal. In certain embodiments, the first control circuitry is configured to maintain the bipolar analog signal substantially fixed at the zero center point. In some embodiments, the first control circuitry is configured to provide the bipolar analog signal having the zero center point without calibration or trimming. In certain embodiments, the first potential is an output potential that tracks, or is held at, a zero reference potential from another portion of the DAC than the digital-to-analog converter circuitry.

In certain embodiments, at least one of the first and second current signals is substantially maintained at a ground potential. The first and second current signals may be complementary. The DAC may further include second control circuitry configured to maintain the at least one of the first and second current signals substantially at the ground potential. In some embodiments, the first control circuitry includes a servo circuit network coupled to a common node input of the subtractor circuitry and the servo circuit network is operative to maintain the first and the second current signals at substantially the same potential. In certain embodiments, the servo network includes an amplifier having a first input coupled to a compensation network and to one of the first and second current signals, a second input coupled to the bipolar current signal and to another one of the first and second current signals, and an output coupled to the common node input of the subtractor circuitry and to an output of the capacitor. The subtractor circuit may include a current mirror network. In some embodiments, the DAC includes one or more R-2R circuit networks, string DACs, or binary weighted current steered DACs. The digital-to-analog circuitry may include a plurality of resistors and a plurality of capacitors in a precision resistor network. In certain embodiments, the DAC is included in a monolithic integrated circuit chip. In some embodiments, the DAC is included in a point-of-care diagnostic device.

In another aspect, a diagnostic system for performing electrochemical detection of a target analyte includes the DAC, processor circuitry configured to receive the digital data and to provide a digital setpoint value indicative of a reference signal to be applied to a counter electrode in electrical contact with the target analyte, wherein the analog output signal of the DAC is indicative of the digital setpoint value, and servoing loop circuitry configured to receive the analog output signal and to apply, in response to the signal, a potential to the counter electrode. In yet another aspect, a method for converting digital data includes a series of binary digits to a bipolar analog signal using the precision digital-to-analog converter (DAC) previously described.

BRIEF DESCRIPTION OF THE DRAWINGS

The foregoing and other objects and advantages will be apparent upon consideration of the following detailed description, taken in conjunction with the accompanying drawings, in which like reference characters refer to like parts throughout, and in which.

DETAILED DESCRIPTION

This disclosure relates generally to a precision bipolar DAC that provides a bipolar output having a substantially fixed center point. To provide an overall understanding of the systems, devices, and methods described herein, certain illustrative embodiments will be described. It is to be understood that the systems, devices, and methods disclosed herein, while shown for use in medical diagnostic systems, may also be employed in general-purpose circuits, including in a monolithic integrated circuit for use in combination with specialized or general-purpose control circuitry. In one aspect, the precision DAC topology provides a bipolar current output having a guaranteed zero point accuracy using low cost components. A fixed center point at zero ensures that a digital input corresponding to zero causes the DAC to supply an analog output of zero. Illustrative implementations exploit matched sets of components that do not themselves require absolute accuracy. Use of current output, rather than voltage output, in certain implementations, provides additional EMI advantages in precision systems. The DAC may be more easily incorporated in a monolithic integrated circuit on a single chip than conventional designs, due in part, to the elimination, in certain implementations, of a separate trimming requirement.

According to one aspect, a precision digital-to-analog converter (DAC) for converting digital data including a series of binary digits to a bipolar analog signal includes digital-to-analog conversion circuitry, subtractor circuitry, and one or more control circuitry. The digital-to-analog conversion circuitry is configured to provide first and second current signals responsive to a digital word indicative of the digital data. The subtractor circuitry is electrically coupled to the digital-to-analog circuitry and configured to provide a bipolar current output signal by subtracting the second current signal from the first current signal. The control circuitry is electrically coupled to the subtractor circuitry and to modify the second potential so that it equals the first potential.

Figure 1:
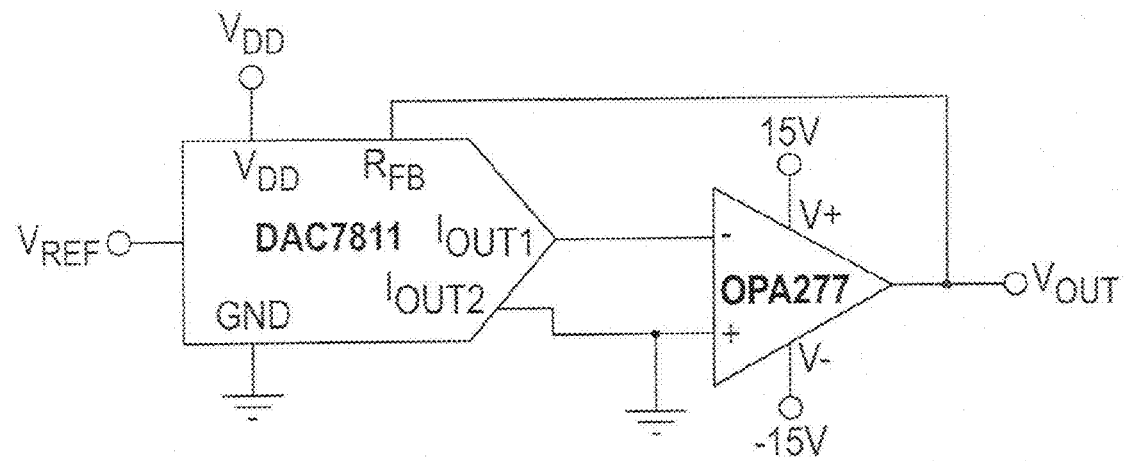
FIG. 1 depicts a conventional digital-to-analog converter in a voltage output configuration.

FIG. 1 depicts a conventional digital-to-analog converter in a voltage output configuration, according to some implementations. In conventional DAC topologies, a trimming element, such as a carefully-manufactured or carefully-selected feedback resistor $R_{fb}$, provides absolute scaling of the current output of DAC 102. Such conventional DAC circuits achieve bipolar voltage output from a pair of unipolar current outputs by offsetting the potential of the $I_{OUT2}$ pin or by level shifting the final voltage output, $V_{OUT}$. The use of the feedback resistor in this architecture introduces a costly trimming step which is prone to drift due to temperature, component aging and power supply variations. Additionally, offsetting the potential of the $I_{OUT2}$ pin instead of holding it stiffly at ground potential introduces conversion accuracy problems that make bipolar output more difficult to implement.

Figure 2:
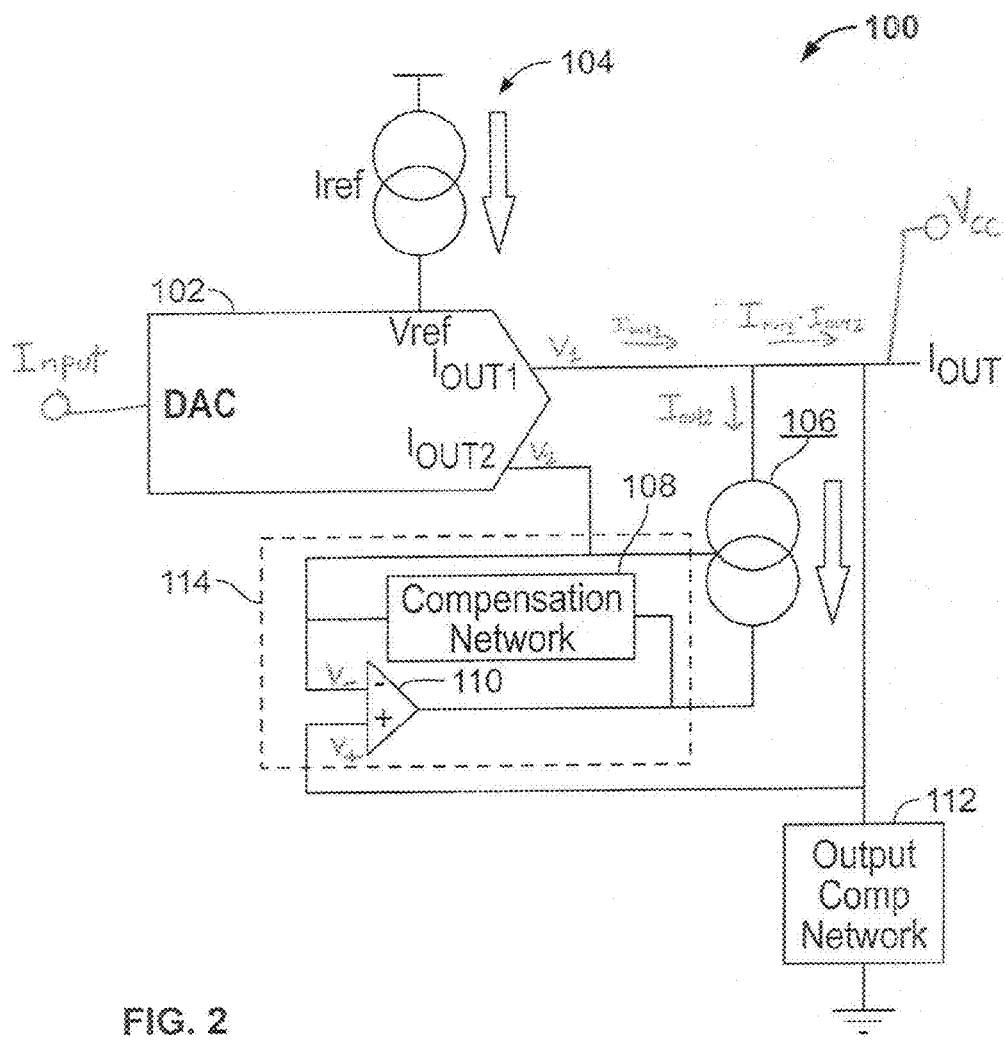
FIG. 2 shows an illustrative precision DAC, according to some implementations.

FIG. 2 shows an illustrative precision DAC 100 according to some implementations. In this example, DAC 100 is configured to provide a an analog current output. The output has a substantially fixed center point at approximately zero. The DAC 100 includes a conventional DAC 102 that receives a reference signal 104 and a digital input signal. The reference signal 104 is a current or voltage signal that is representative of a full scale output. The DAC 102 provides current outputs $I_{OUT1}$ and $I_{OUT2}$ based on the digital input and (optionally) the reference signal. $I_{OUT1}$ has a first potential $v_1$, and $I_{OUT2}$ has a second potential $v_2$. The first potential $v_1$ has the same potential as the node $I_{OUT}$. The first potential $v_1$ may be set by another component or ciruciut outside of the DAC 100, such as a transimpedance stage or a connection to virtual ground. The DAC 102 can be any suitable conventional digital-to-analog converter that uses digital-to-analog converter circuitry. For example, the DAC 102 can be a single- or multi-bit serial-input digital-to-analog converter that provides current outputs.

According to one aspect, subtractor circuitry 106 is coupled to receive the outputs of the DAC 102 and to provide a bipolar output current signal based on the received signals $I_{OUT1}$ and $I_{OUT2}$. In this manner, the topology in system 100 is capable of providing a bipolar output having a center point that is substantially fixed at zero, thereby improving the accuracy of the output signal. The subtractor circuitry 106 subtracts the positive (complementary) current outputs $I_{OUT1}$ and $I_{OUT2}$ from each other. The output of the subtractor circuit 106, $I_{OUT1}$-$I_{OUT2}$, is a bipolar current signal that is indicative of an analog equivalent of the digital data. Center point accuracy is ensured by the circuit's dependence on $I_{OUT1}$/$I_{OUT2}$ split accuracy and the symmetry of the current mirror, both of which are highly accurate due to modern fabrication practices. In order to improve the precision of the output signal, control circuitry 114 is employed to maintain $I_{OUT1}$ and $I_{OUT2}$ as specified potentials (e.g., ground potential or the potential of a power supply). In this example, the control circuitry 114 includes a compensation network 108 (e.g., a capacitor) and an amplifier 110 coupled between $I_{OUT2}$ and the subtractor circuitry 106. However, other suitable servo loops may be used.

Figure 3:
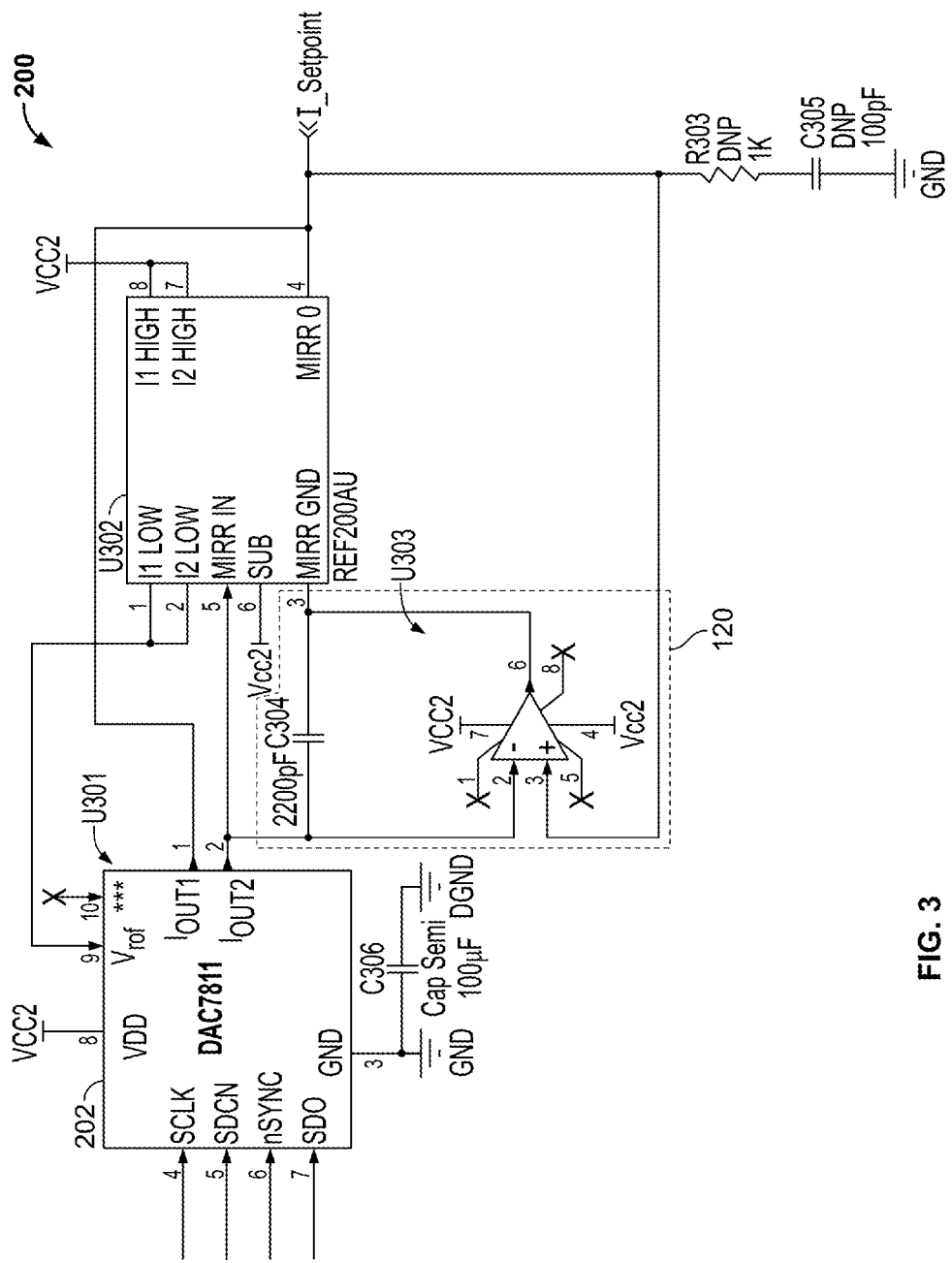
FIG. 3 shows a schematic of an illustrative precision DAC configured to provide a bipolar current output with a fixed center point at zero, according to some implementations.

FIG. 3 shows a schematic of an illustrative precision DAC 200 configured to provide a bipolar current output with a fixed center point at zero, according to some implementations. The digital-to-analog converter circuitry 202 is similar to DAC circuitry 102 (FIG. 1). In this example, the DAC 202 is a 12-bit, serial-input, current-output, digital-to-analog (DAC) converter operating from a single 3-V to 5-V power supply. DAC 202 is a conventional off-the-shelf converter that is typically used in digital converters to provide a current output and is typically connected to a current to voltage (I/V) convertor (scaled by feedback resistor $R_{FB}$). However, DAC 202 is configured differently in precision DAC 200. In certain implementations, instead of being coupled to an I/V converter, the outputs $I_{OUT1}$ and $I_{OUT2}$ of the DAC 202 are provided to a current mirror U302 in system 200. The current mirror U302 subtracts the positive complementary current outputs $I_{OUT1}$ and $I_{OUT2}$ from each other to provide an initial bipolar output without offsetting the potentials or level-shifting the final output. The current mirror U302 can be any conventional current mirror having suitably matched components. The node I_setpoint is held at ground potential by the circuit (not shown) being driven by precision DAC 200. In order to maintain the current split accuracy, in some implementations, $I_{OUT1}$ is also held at ground potential. This is done by servoing the common node of the current mirror (pin 3 of current mirror 104) using servo loop 120, which includes amplifier U303 and capacitor C304.

In some implementations, accuracy is further improved by eliminating ground point voltage errors through careful layout. For example, ground point voltage errors may be reduced or eliminated by a tightly coupled ohmic connection between pin 3 of amplifier U303 and pin1 of DAC 202. The values of resistor R303, capacitor C305 and capacitor C304 are determined by the circuit stability requirements, while selection of amplifier U303 and the dynamic impedance of the circuit are driven by I_Setpoint. The methods used for tuning these components are well known by those skilled in the art. The reference voltage $V_{REF}$ can be fed with a current source, which ensures absolute full scale accuracy. Meanwhile, because the current split ratio of $I_{OUT1}/I_{OUT2}$ and the current mirror 104 is very accurate, the bipolar signal output has a zero center point. Therefore, a digital input corresponding to zero results in an analog output substantially equal to zero. The precision of the output signal depends on the accuracy of the pairing, but not the absolute value of the individual currents. The current mirror accuracy can be relaxed (by a factor of 2), as the $I_{OUT1}/I_{OUT2}$ current split has already assisted in the overall circuit balancing.

Figure 4:
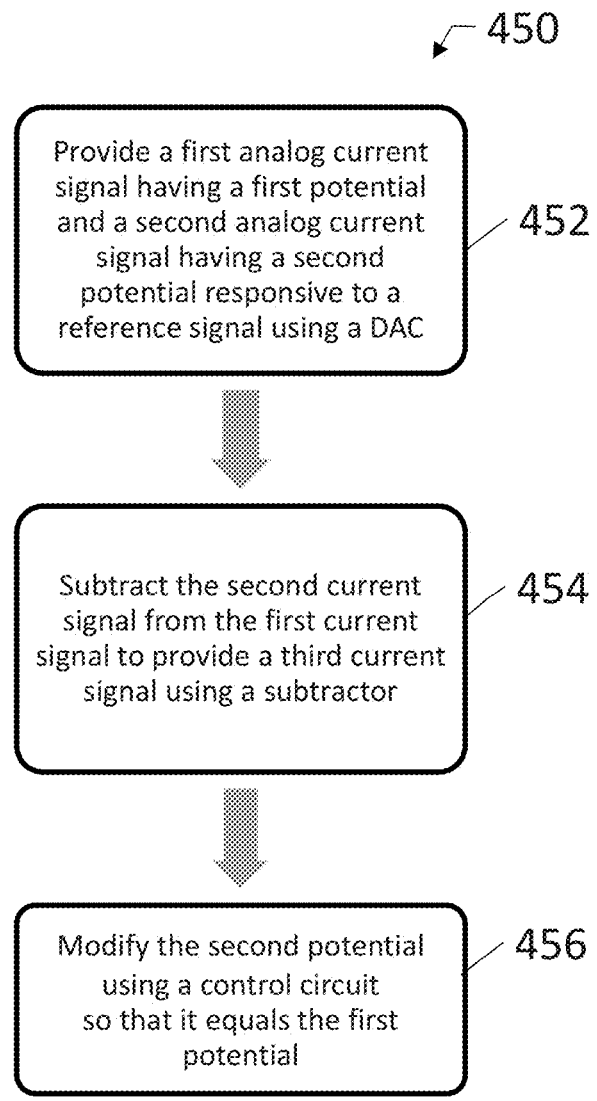
FIG. 4 depicts a flowchart for converting digital data including a series of binary digits to a bipolar analog signal using a precision digital-to-analog converter, according to some implementations.

FIG. 4 depicts a flowchart 450 for converting digital data including a series of binary digits to a bipolar analog signal using a precision digital-to-analog converter, according to some implementations. The method described by flowchart 450 may be implemented using the precision DAC described above. In step 452, first and second analog current signals are provided responsive to a digital word using a DAC (e.g., DAC 102 in FIG. 2). The first analog current signal has a first potential, and the second analog current signal has a second potential. The reference signal may be a series of binary digits, and the current signals provided in response may be a complementary pair of current signals. In step 454, a subtractor subtracts the second analog current signal from the first analog current signal to provide a bipolar current signal. The subtraction may be performed by a current mirror (e.g., current mirror U302 in FIG. 3), or any other suitable subtraction circuitry. In step 456, a control circuit modifies the second potential so that it equals the first potential. Equalizing the potential of the current outputs may improve the split accuracy of the DAC circuitry providing the first and second current signals. Thus, the method described by flowchart 450 may convert a series of digital values to a bipolar analog signal.

The systems, circuits, devices, and methods described above may be incorporated in a diagnostic system for detecting the presence or absence of a target marker using electrocatalytic techniques. Electrochemical techniques including, but not limited to cyclic voltammetry, amperometry, chronoamperometry, differential pulse voltammetry, calorimetry, and potentiometry may be used for detecting a target marker. The precision digital to analog converter may be used to control the signal sweep applied to a sample being tested by electrochemical detection. A brief description of one of these techniques, as applied to the current system, is provided below, it being understood that the electrocatalytic techniques are illustrative and non-limiting and that other techniques can be envisaged for use with the other systems, devices and methods of the current system. Applications of electrocatalytic techniques are described in further detail in U.S. Pat. Nos. 7,361,470 and 7,741,033, and PCT Application No. PCT/US12/024015, which are hereby incorporated by reference herein in their entireties.

Figure 8:
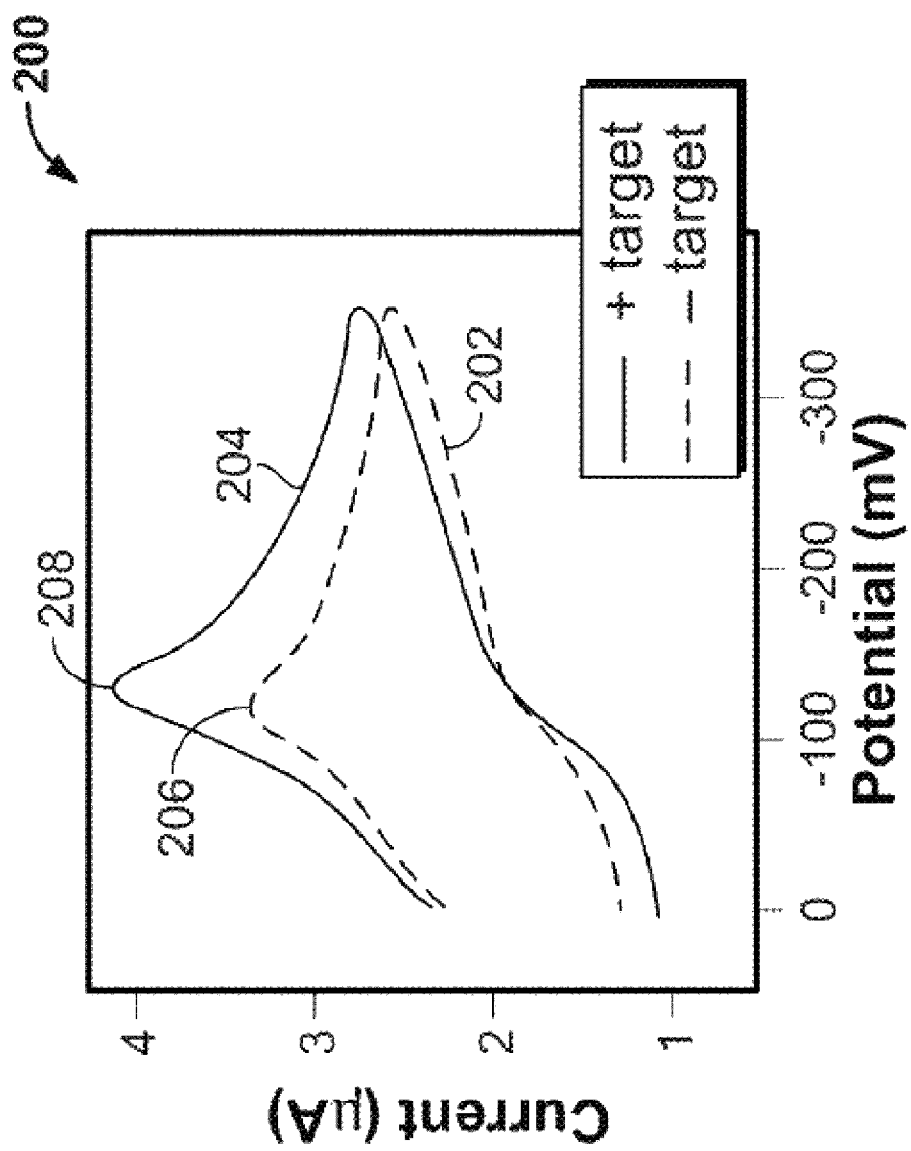
FIG. 8 depicts representative electrocatalytic detection signals.

Chart 200 of FIG. 8 depicts representative electrocatalytic detection signals. A signal generator, such as a potentiostat, is used to apply a voltage signal at an electrode. The signal generator may provide an analog signal output in response to a digital input using the precision DAC disclosed herein. For example, the precision DAC may be used to cycle or ramp the applied voltage between two points, such as from 0 mV to −300 mV and back to 0 mV, while the resultant current is measured. Accordingly, chart 200 depicts the current along the vertical axis at corresponding potentials between 0 mV and −300 mV, along the horizontal axis. Data graph 202 represents a signal measured at an electrode in the absence of a target marker. Data graph 204 represents a signal measured at an electrode in the presence of a target marker. As can be seen on data graph 204, the signal recorded in the presence of the target molecule provides a higher amplitude current signal, particularly when comparing peak 208 with peak 206 located at approximately −100 mV. Accordingly, the presence and absence of the marker can be differentiated.

In certain applications, a single electrode or sensor is configured with two or more probes, arranged next to each other, or on top of or in close proximity within the chamber so as to provide target and control marker detection in an even smaller point-of-care size configuration. For example, a single electrode sensor may be coupled to two types of probes, which are configured to hybridize with two different markers. In certain approaches, a single probe is configured to hybridize and detect two markers. In certain approaches, two types of probes may be coupled to an electrode in different ratios. For example, a first probe may be present on the electrode sensor at a ratio of 2:1 to the second probe. Accordingly, the sensor is capable of providing discrete detection of multiple analytes. For example, if the first marker is present, a first discrete signal (e.g., current) magnitude would be generated, if the second marker is present, a second discrete signal magnitude would be generated, if both the first and second marker are present, a third discrete signal magnitude would be generated, and if neither marker is present, a fourth discrete signal magnitude would be generated. Similarly, additional probes could also be implemented for increased numbers of multi-target detection.

Figure 9:
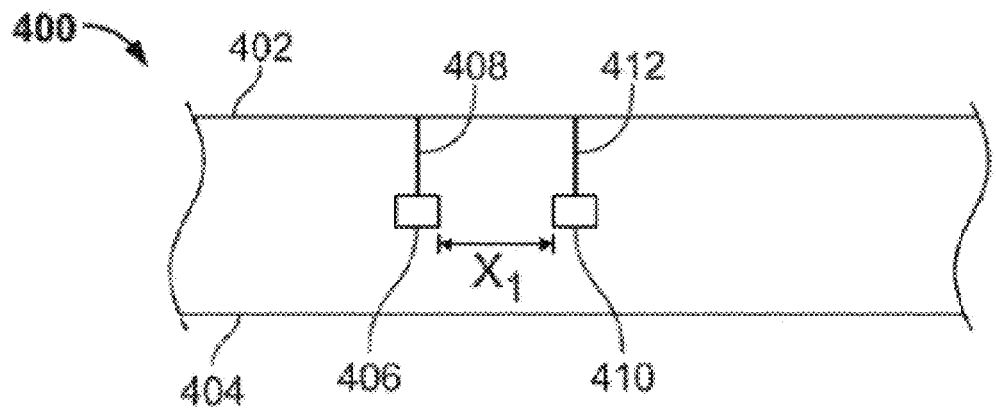
FIG. 9 depicts an analysis chamber with a pathogen sensor and a host sensor.

In certain aspects, the sensors and electrodes described herein are integrated into a sensing or analysis chamber, for example in a point-of-care device, to analyze a sample from a biological host. FIG. 9 depicts an analysis chamber 400 with a pathogen sensor 406 and a host sensor 410. The chamber 400 includes walls 402 and 404 that form a space with which a sample is retained and analyzed at sensors 406 and 410. Pathogen sensor 406 includes a conductive trace 408 to connect the sensor 406 to controlling instrumentation such as a potentiostat. Host sensor 410 is also connected to external or controlling instrumentation with a conductive trace 412. Pathogen sensor 406 and host sensor 410 are separated by a distance $X_1$.

Figure 10:
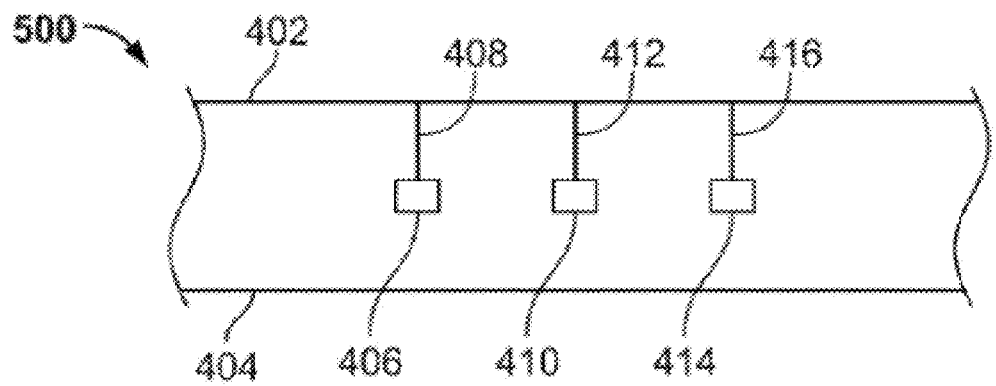
FIG. 10 depicts an analysis chamber with a pathogen sensor and a host sensor.

In certain aspects, the systems, methods, and devices described herein are integrated into a sensing or analysis chamber, for example in a point-of-care device, to analyze a sample from a biological host. FIG. 10 depicts an analysis chamber 400 with a pathogen sensor 406 and a host sensor 410. The chamber 400 includes walls 402 and 404 that form a space with which a sample is retained and analyzed at sensors 406 and 410. Pathogen sensor 406 includes a conductive trace 408 to connect the sensor 406 to controlling instrumentation such as a potentiostat. Host sensor 410 is also connected to external or controlling instrumentation with a conductive trace 412. Pathogen sensor 406 and host sensor 410 are separated by a distance $X_1$.

The pathogen sensor 406 is used to determine whether or not the marker is present in the sample. Although not depicted in FIG. 10, pathogen sensor 406 includes a probe configured to couple to a target marker from a pathogen. In certain approaches, the probe is a peptide nucleic acid probe. For example, the probe coupled to the pathogen sensor 406 may include a nucleotide sequence that is complementary to a nucleotide sequence from a pathogen which is unique to that pathogen.

The host sensor 410 includes a probe configured to couple to a host marker. The host marker is an endogenous element from a biological host, such as a DNA sequence, RNA sequence, or peptide. For example, the probe coupled to host sensor 410 may be configured with a nucleotide sequence that hybridizes with a nucleotide sequence unique to the human genome. In certain approaches, the probe for the host marker is a peptide nucleic acid probe. Preferably, the host marker is present in every biological sample taken from a human patient, and therefore can serve as a positive, internal control for the analysis process. Accordingly, detection of the host marker at host sensor 410 serves as a control for the assay. Specifically, detection of the host marker confirms that the sample was taken correctly from the host (e.g., a patient), that the sample was processed correctly, and that hybridization of the probe and marker in the analysis chamber has taken place successfully. If any part of the assay fails, and the host marker is not detected at host sensor 410, the assay is considered indeterminate.

The pathogen sensor 406 and host sensor 410 operate using the electrocatalytic methods described in detail in U.S. Pat. Nos. 7,361,470 and 7,741,033, and PCT Application No. PCT/US12/024015 (although such sensors and the internal control techniques discussed herein could also be applied in other diagnostic methods). FIG. 10 depicts only two sensors, but any number of sensors may be used. For example, chamber 400 may include a plurality of pathogen sensors 406 and a plurality of host sensors 410. When a plurality of sensors is used, each sensor may optionally be configured to sense a different target marker in order to detect the presence or absence of different pathogens, different hosts, or different parts of the same pathogen or the same host. In alternative approaches, a plurality of pathogen sensors 406 is used, but each pathogen sensor is configured to sense the same target marker in order to provide additional verification of the presence or absence of that target marker. Similarly, a plurality of host sensors 410 may also be used with each sensor being configured to detect the presence or absence of the same host target marker to provide additional verification of the measurement.

Figure 5:
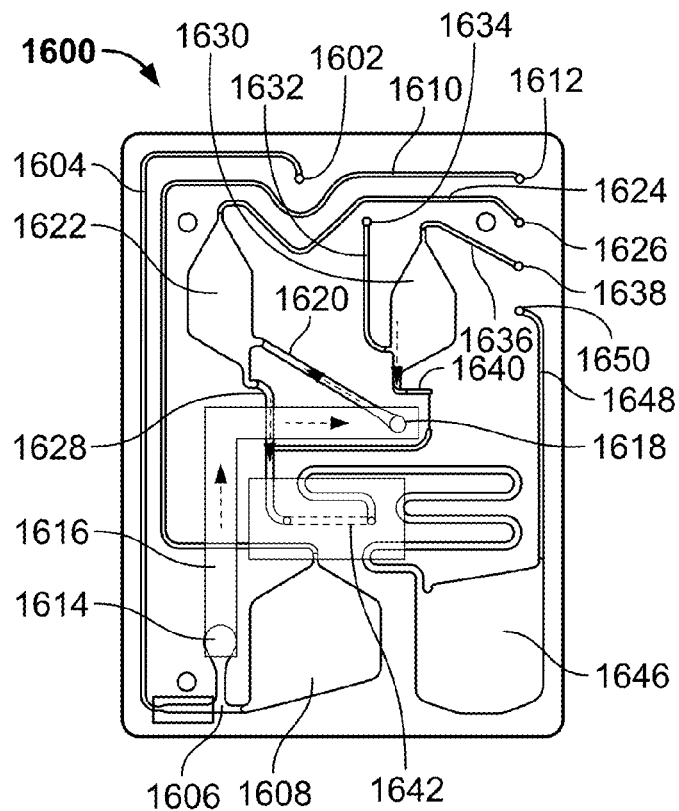
FIG. 5 depicts a cartridge system for receiving, preparing, and analyzing a biological sample, according to some implementations.
Figure 11:
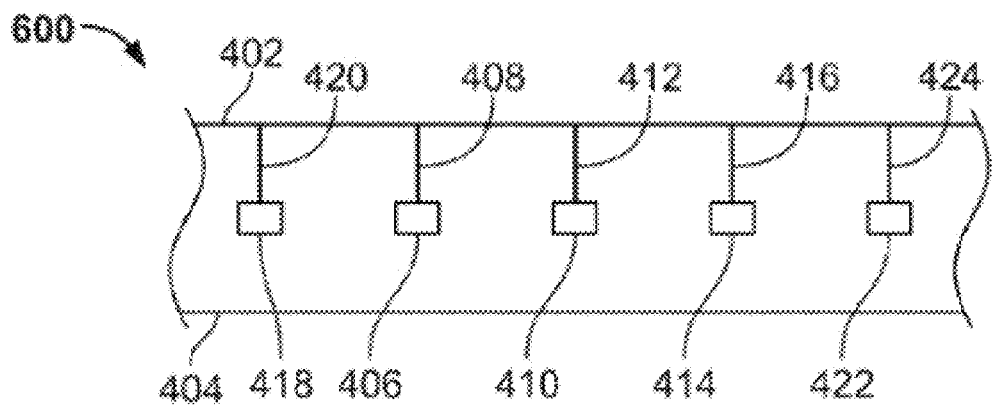
FIG. 11 depicts an additional embodiment of an analysis chamber.

FIG. 11 depicts an additional embodiment of an analysis chamber. Chamber 500 is similar to chamber 400 in that it includes walls 402 and 404, pathogen sensor 406 and host sensor 410. Chamber 500 additionally includes a non-sense sensor 414. Similar to pathogen sensor 406 and host sensor 410, non-sense sensor 414 is electrically coupled to controlling instrumentation, such as a potentiostat, with a conductive trace 416. The non-sense sensor 414 may also include an electrode, such as a nanostructured microelectrode. Non-sense sensor 414 includes a probe, such as probe 106. In certain approaches, the non-sense probe is a peptide nucleic acid probe. The non-sense probe, however, is not configured to mate with a marker from the pathogen or the biological host. Instead, the probe coupled to non-sense sensor 414 has a structure, such as a nucleotide sequence, which is not found in either the pathogen or the biological host. The non-sense sensor serves as an additional control to verify that the conditions within analysis chamber 500 can provide accurate sensing results. Non-sense sensor 414 tests for nonspecific binding. Nonspecific binding of a nucleotide sequence may occur under inappropriate hybridization conditions in chamber 500. For example, nonspecific binding may occur when the pH, ionic strength, or temperature are not appropriate for accurate testing. If binding occurs at non-sense sensor 414, then other nonspecific binding may take place at pathogen sensor 406 and the host sensor 410, and therefore the assay would be inaccurate. The non-sense sensor 414 is thereby able to act as an additional control for testing conditions. The non-sense sensor 414 may also function using electrocatalytic techniques as previously described. Although FIG. 5 depicts three sensors, any number of sensors could be used. Sensors 406, 410, and 414 are arranged in chamber 500 in a linear arrangement. However, sensors 406, 410, and 414 may also be arranged in other patterns.

Figure 6:
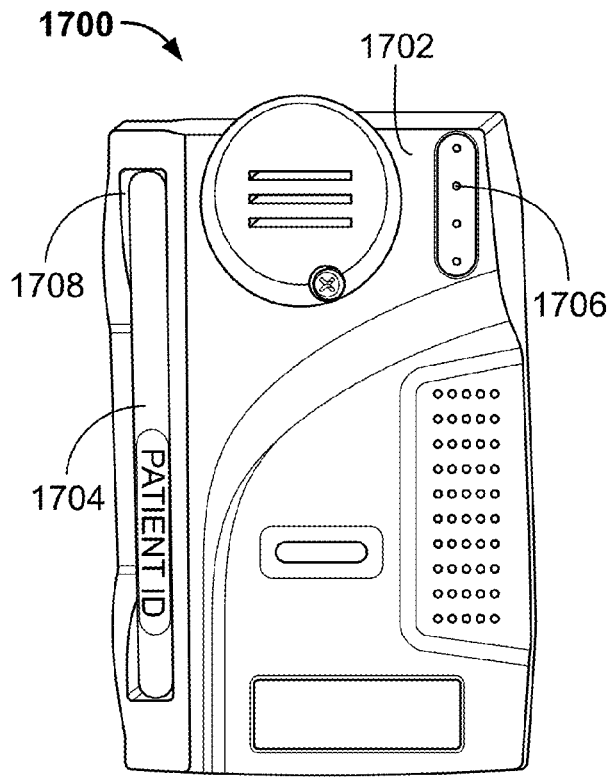
FIG. 6 depicts a cartridge for an analytical detection system, according to some implementations.

FIG. 6 depicts an additional embodiment of an analysis chamber 600 which is similar to chambers 400 and 500 previously described. FIG. 6 also depicts a reference electrode 418 and a counter electrode 422. The reference electrode 418 and counter electrode 422 are connected to the controlling instrumentation (e.g., a potentiostat driven by a precision DAC) by conductive traces 420 and 424, respectively. The reference electrode 418 and counter electrode 422 are used in the electrocatalytic measurements. The reference electrode 418 serves as a reference for applying a voltage at any of the sensors 406, 410, and 414. When a voltage is applied at a sensor (e.g., sensors 406, 410, and 414), the current generated flows through a sensor (e.g., sensors 406, 410, and 414), through the hybridized complex of the probe and target, through the sample, and through the counter electrode 422.

The systems, circuits, devices, and methods described above may be incorporated in a diagnostic system that includes a cartridge to prepare a sample for analysis and perform a detection analysis. FIG. 5 depicts a cartridge system 1600 for receiving, preparing, and analyzing a biological sample. For example, cartridge system 1600 may be configured to remove a portion of a biological sample from a sample collector or swab, transport the sample to a lysis zone where a lysis and fragmentation procedure is performed, and transport the sample to an analysis chamber for determining the presence of various markers and to determine a disease state of a biological host.

FIG. 6 depicts an embodiment of a cartridge for an analytical detection system. Cartridge 1700 includes an outer housing 1702, for retaining a processing and analysis system, such as system 1600. Cartridge 1700 allows the internal processing and analysis system to integrate with other instrumentation. Cartridge 1700 includes a receptacle 1708 for receiving a sample container 1704. A sample is received from a patient, for example, with a swab. The swab is then placed into container 1704. Container 1704 is then positioned within receptacle 1708. Receptacle 1708 retains the container and allows the sample to be processed in the analysis system. In certain approaches, receptacle 1708 couples container 1704 to port 1602 so that the sample can be directed from container 1704 and processed though system 1600. Cartridge 1700 may also include additional features, such as ports 1706, for ease of processing the sample.

Cartridges may use any appropriate formats, materials, and size scales for sample preparation and sample analysis. In certain approaches, cartridges use microfluidic channels and chambers. In certain approaches, the cartridges use macrofluidic channels and chambers. Cartridges may be single layer devices or multilayer devices. Methods of fabrication include, but are not limited to, photolithography, machining, micromachining, molding, and embossing.

Figure 7:
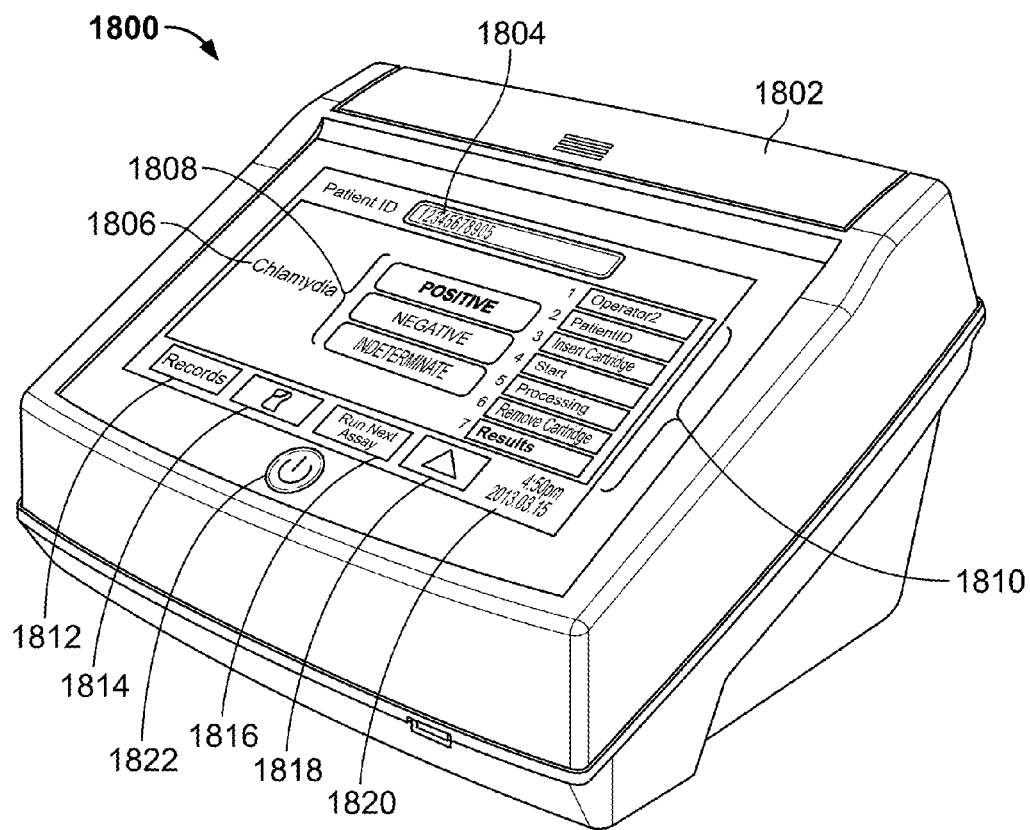
FIG. 7 depicts an automated testing system, according to some implementations.

FIG. 7 depicts an automated testing system to provide ease of processing and analyzing a sample. System 1800 may include a cartridge receiver 1802 for receiving a cartridge, such as cartridge 1700. System 1800 may include other buttons, controls, and indicators. For example, indicator 1804 is a patient ID indicator, which may be typed in manually by a user, or read automatically from cartridge 1700 or cartridge container 1704. System 1800 may include a "Records" button 1812 to allow a user to access or record relevant patient record information, "Print" button 1814 to print results, "Run Next Assay" button 1818 to start processing an assay, "Selector" button 1818 to select process steps or otherwise control system 1800, and "Power" button 1822 to turn the system on or off. Other buttons and controls may also be provided to assist in using system 1800. System 1800 may include process indicators 1810 to provide instructions or to indicate progress of the sample analysis. System 1800 includes a test type indicator 1806 and results indicator 1808. For example, system 1800 is currently testing for *Chlamydia* as shown by indicator 1806, and the test has resulted in a positive result, as shown by indicator 1808. System 1800 may include other indicators as appropriate, such as time and date indicator 1820 to improve system functionality.

The foregoing is merely illustrative of the principles of the disclosure, and the systems, devices, and methods can be practiced by other than the described embodiments, which are presented for the purposes of illustration and not of limitation. It is to be understood that the systems, devices, and methods disclosed herein, while shown for use in detection systems for bacteria, and specifically, for *Chlamydia Trachomatis*, may be applied to systems, devices, and methods to be used in other applications including, but not limited to, detection of other bacteria, viruses, fungi, prions, plant matter, animal matter, protein, RNA sequences, DNA sequences, as well as cancer screening and genetic testing, including screening for genetic disorders.

Variations and modifications will occur to those of skill in the art after reviewing this disclosure. The disclosed features may be implemented, in any combination and subcombination (including multiple dependent combinations and subcombinations), with one or more other features described herein. The various features described or illustrated above, including any components thereof, may be combined or integrated in other systems. Moreover, certain features may be omitted or not implemented.

Examples of changes, substitutions, and alterations are ascertainable by one skilled in the art and could be made without departing from the scope of the information disclosed herein. All references cited are hereby incorporated by reference herein in their entireties and made part of this application.

What is claimed is:

1. A precision digital-to-analog converter (DAC) for converting digital data to a bipolar analog signal, comprising:

digital-to-analog converter circuitry configured to provide, responsive to digital input data, a first analog current signal having a first potential set by a voltage source external to the DAC, and a second analog current signal having a second potential;

subtractor circuitry configured to provide a bipolar current signal by subtracting the second analog current signal from the first analog current signal, the bipolar current signal having a zero center point; and first control circuitry electrically coupled to the subtractor circuitry and to the digital-to-analog converter circuitry, and configured to modify the second potential so that the second potential equals the first potential.

2. The DAC of claim 1, wherein the DAC is configured to provide the bipolar current signal having the zero center point without calibration or trimming.

3. The DAC of claim 1, wherein at least one of the first and second analog current signals is substantially maintained at a ground source.

4. The DAC of claim 3, further comprising second control circuitry configured to maintain the stability of the bipolar current signal.

5. The DAC of claim 1, wherein the first control circuitry comprises a servo circuit network coupled to a common node input of the subtractor circuity, the servo circuit being operative to maintain the first and the second current signals at substantially the same potential.

6. The DAC of claim 5, wherein the servo network comprises an amplifier having a first input coupled to a compensation network and to one of the first and second current signals, a second input coupled to the bipolar current signal and to another one of the first and second current signals, and an output coupled to the common node input of the subtractor circuitry and to an output of the compensation network.

7. The DAC of claim 1, wherein the first and second analog current signals are complementary.

8. The DAC of claim 1, wherein the digital-to-analog converter circuitry comprises one or more R-2R circuit networks, string digital-to-analog converters, or binary weighted current steered digital-to-analog converters.

9. The DAC of claim 1, wherein the digital-to-analog converter circuitry comprises a plurality of resistors and a plurality of capacitors in a precision resistor network.

10. The DAC of claim 1, where the first potential tracks a zero reference potential.

11. The DAC of claim 1, where the first potential is held at a zero reference potential.

12. A point-of-care diagnostic device comprising the DAC of claim 1.

13. The DAC of claim 1, wherein the subtractor circuit comprises a current mirror network.

14. A diagnostic system for performing electrochemical detection of a target analyte, the system comprising:

the DAC according to claim 1;

processor circuitry configured to receive the digital data, and to provide a digital setpoint value indicative of a reference signal to be applied to a counter electrode in electrical contact with the target analyte, wherein the binary analog signal of the DAC is indicative of the digital setpoint value: and servoing loop circuitry configured to receive the binary analog signal and to apply, in response to the binary analog signal, a potential to the counter electrode.

15. A precision digital-to-analog converter (DAC) for converting digital data to a bipolar analog signal, comprising:

digital-to-analog converter circuitry configured to provide, responsive to digital input data, a first analog current signal having a first potential and a second analog current signal having a second potential;

subtractor circuitry configured to provide a bipolar current signal by subtracting the second analog current signal from the first analog current signal, the bipolar current signal having a zero center point; and first control circuitry electrically coupled to the subtractor circuitry and to the digital-to-analog converter circuitry, and configured to modify the second potential so that the second potential equals the first potential;

wherein the DAC is configured to provide the bipolar current signal having the zero center point without calibration or trimming.

16. A precision digital-to-analog converter (DAC) for converting digital data to a bipolar analog signal, comprising:

digital-to-analog converter circuitry configured to provide, responsive to digital input data, a first analog current signal having a first potential and a second analog current signal having a second potential, at least one of the first and second analog current signals substantially maintained at a ground potential;

subtractor circuitry configured to provide a bipolar current signal by subtracting the second analog current signal from the first analog current signal, the bipolar current signal having a zero center point; and first control circuitry electrically coupled to the subtractor circuitry and to the digital-to-analog converter circuitry, and configured to modify the second potential so that the second potential equals the first potential.

17. The DAC of claim 16, further comprising second control circuitry configured to maintain the stability of the bipolar current signal.

18. A precision digital-to-analog converter (DAC) for converting digital data to a bipolar analog signal, comprising:

digital-to-analog converter circuitry configured to provide, responsive to digital input data, a first analog current signal having a first potential and a second analog current signal having a second potential;

subtractor circuitry configured to provide a bipolar current signal by subtracting the second analog current signal from the first analog current signal, the bipolar current signal having a zero center point; and first control circuitry electrically coupled to the subtractor circuitry and to the digital-to-analog converter circuitry, the first control circuitry including a servo circuit network coupled to a common note input of the subtractor circuitry, the servo circuit network configured to modify the second potential so that the second potential equals the first potential.

19. The DAC of claim 18, wherein the servo network comprises an amplifier having a first input coupled to a compensation network and to one of the first and second current signals, a second input coupled to the bipolar current signal and to another one of the first and second current signals, and an output coupled to the common node input of the subtractor circuitry and to an output of the compensation network.

20. A precision digital-to-analog converter (DAC) for converting digital data to a bipolar analog signal, comprising:

digital-to-analog converter circuitry configured to provide, responsive to digital input data, a first analog current signal having a first potential and a second analog current signal having a second potential, the first and second analog current signals being complementary;

subtractor circuitry configured to provide a bipolar current signal by subtracting the second analog current signal from the first analog current signal, the bipolar current signal having a zero center point; and first control circuitry electrically coupled to the subtractor circuitry and to the digital-to-analog converter circuitry, and configured to modify the second potential so that the second potential equals the first potential.

21. A precision digital-to-analog converter (DAC) for converting digital data to a bipolar analog signal, comprising:

digital-to-analog converter circuitry including one or more R-2R circuit networks, string digital-to-analog converters, or binary weighted current steered digital-to-analog converters, the digital-to-analog converter circuitry configured to provide, responsive to digital input data, a first analog current signal having a first potential and a second analog current signal having a second potential;

subtractor circuitry configured to provide a bipolar current signal by subtracting the second analog current signal from the first analog current signal, the bipolar current signal having a zero center point; and first control circuitry electrically coupled to the subtractor circuitry and to the digital-to-analog converter circuitry, and configured to modify the second potential so that the second potential equals the first potential.

22. A precision digital-to-analog converter (DAC) for converting digital data to a bipolar analog signal, comprising:

digital-to-analog converter circuitry including a plurality of resistors and a plurality of capacitors in a precision resistor network, the digital-to-analog converter circuitry configured to provide, responsive to digital input data, a first analog current signal having a first potential and a second analog current signal having a second potential;

subtractor circuitry configured to provide a bipolar current signal by subtracting the second analog current signal from the first analog current signal, the bipolar current signal having a zero center point; and first control circuitry electrically coupled to the subtractor circuitry and to the digital-to-analog converter circuitry, and configured to modify the second potential so that the second potential equals the first potential.

23. A precision digital-to-analog converter (DAC) for converting digital data to a bipolar analog signal, comprising:

digital-to-analog converter circuitry configured to provide, responsive to digital input data, a first analog current signal having a first potential that tracks a zero reference potential from a voltage source external to the DAC, and a second analog current signal having a second potential;

subtractor circuitry configured to provide a bipolar current signal by subtracting the second analog current signal from the first analog current signal, the bipolar current signal having a zero center point; and first control circuitry electrically coupled to the subtractor circuitry and to the digital-to-analog converter circuitry, and configured to modify the second potential so that the second potential equals the first potential.

24. A precision digital-to-analog converter (DAC) for converting digital data to a bipolar analog signal, comprising:
- digital-to-analog converter circuitry configured to provide, responsive to digital input data, a first analog current signal having a first potential held at the zero reference potential from a voltage source external to the DAC, and a second analog current signal having a second potential;
- subtractor circuitry configured to provide a bipolar current signal by subtracting the second analog current signal from the first analog current signal, the bipolar current signal having a zero center point; and
- first control circuitry electrically coupled to the subtractor circuitry and to the digital-to-analog converter circuitry, and configured to modify the second potential so that the second potential equals the first potential.

25. A point-of-care diagnostic device comprising:
- a digital-to-analog converter (DAC) for converting digital data to a bipolar analog signal, comprising:
  - digital-to-analog converter circuitry configured to provide, responsive to digital input data, a first analog current signal having a first potential and a second analog current signal having a second potential;
  - subtractor circuitry configured to provide a bipolar current signal by subtracting the second analog current signal from the first analog current signal, the bipolar current signal having a zero center point; and
  - first control circuitry electrically coupled to the subtractor circuitry and to the digital-to-analog converter circuitry, and configured to modify the second potential so that the second potential equals the first potential.

26. A precision digital-to-analog converter (DAC) for converting digital data to a bipolar analog signal, comprising:
- digital-to-analog converter circuitry configured to provide, responsive to digital input data, a first analog current signal having a first potential and a second analog current signal having a second potential;
- subtractor circuitry including a current mirror network configured to provide a bipolar current signal by subtracting the second analog current signal from the first analog current signal, the bipolar current signal having a zero center point; and
- first control circuitry electrically coupled to the subtractor circuitry and to the digital-to-analog converter circuitry, and configured to modify the second potential so that the second potential equals the first potential.

27. A diagnostic system for performing electrochemical detection of a target analyte, the system comprising:
- a precision digital-to-analog converter (DAC) for converting digital data to a bipolar analog signal, comprising:
  - digital-to-analog converter circuitry configured to provide, responsive to digital input data, a first analog current signal having a first potential and a second analog current signal having a second potential;
  - subtractor circuitry configured to provide a bipolar current signal by subtracting the second analog current signal from the first analog current signal, the bipolar current signal having a zero center point; and
  - first control circuitry electrically coupled to the subtractor circuitry and to the digital-to-analog converter circuitry, and configured to modify the second potential so that the second potential equals the first potential;
- processor circuitry configured to receive the digital data, and to provide a digital setpoint value indicative of a reference signal to be applied to a counter electrode in electrical contact with the target analyte, wherein the binary analog signal of the DAC is indicative of the digital setpoint value; and
- servoing loop circuitry configured to receive the binary analog signal and to apply, in response to the binary analog signal, a potential to the counter electrode.

* * * * *